United States Patent
Miyake et al.

(10) Patent No.: US 11,685,703 B2
(45) Date of Patent: Jun. 27, 2023

(54) PROCESS FOR PREPARING A 3,7-DIMETHYLALKANE COMPOUND

(71) Applicant: Shin-Etsu Chemical Co., Ltd., Tokyo (JP)

(72) Inventors: Yuki Miyake, Joetsu (JP); Takeru Watanabe, Joetsu (JP); Takeshi Kinsho, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 18/058,316

(22) Filed: Nov. 23, 2022

(65) Prior Publication Data

US 2023/0159412 A1    May 25, 2023

(30) Foreign Application Priority Data

Nov. 25, 2021 (JP) .............................. JP2021-191182

(51) Int. Cl.
   *C07C 5/44* (2006.01)
(52) U.S. Cl.
   CPC ...................................... *C07C 5/44* (2013.01)
(58) Field of Classification Search
   CPC ........................................................ C07C 5/44
   See application file for complete search history.

(56) References Cited

PUBLICATIONS

Barros-Parada et al. "3,7-Dimethylpentadecane: a Novel Sex Pheromone Component from Leucoptera sinuella (Lepidoptera: Lyonetiidae)" Journal of Chemical Ecology, 46(9):820-829 (2020).

*Primary Examiner* — Thuan D Dang
(74) *Attorney, Agent, or Firm* — Myers Bigel, P.A.

(57) ABSTRACT

The present invention relates to a process for preparing a 3,7-dimethylalkane compound (3): wherein n is 5 or 6, the process comprising: subjecting a nucleophilic reagent, 2,6-dimethyloctyl compound (1): wherein $M^1$ represents Li, Mg $Z^1$, $CuZ^1$, or $CuLiZ^1$, wherein $Z^1$ represents a halogen atom or a 2,6-dimethyloctyl group, to a coupling reaction with an electrophilic alkyl reagent (2): wherein $X^1$ represents a halogen atom or a p-toluenesulfonate group, and "n" is as defined above, to form the 3,7-dimethylalkane compound (3).

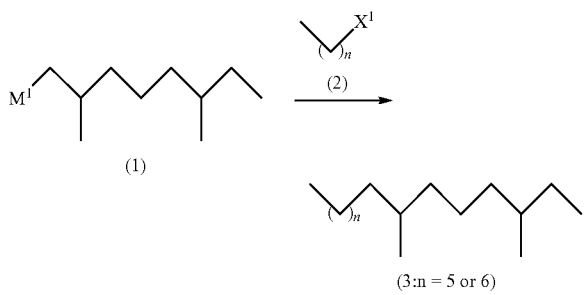

2 Claims, No Drawings

PROCESS FOR PREPARING A 3,7-DIMETHYLALKANE COMPOUND

TECHNICAL FIELD

The present invention relates to a process for preparing a 3,7-dimethylalkane compound. More specifically, the present invention relates to processes for preparing, among 3,7-dimethylalkane compounds, 3,7-dimethylpentadecane and 3,7-dimethyltetradecane, respectively, both of which are a sex pheromone of *Leucoptera sinuella* (scientific name), a pest of poplar (*Populus* spp.) and other plants.

BACKGROUND ART

*Leucoptera sinuella* is one of the most serious pests of poplar and willow (*Salix* spp.), both of which are a raw material of wood. The larvae of *Leucoptera sinuella* mine and eat the inside of leaves, inhibiting photosynthesis of their hosts. Moreover, the grown larvae can migrate to neighboring fruit trees such as apple and orange. Recently, fruits exported from Chile have been frequently rejected in their importer countries because *Leucoptera sinuella* is designated as a quarantine pest. Neither traditional pest control methods with pesticides nor eco-friendly, biological control methods have been developed for this pest, and thus mating disruption using sex pheromones is expected to be a promising control method (Non-Patent Literature 1, as listed below).

The sex pheromone of *Leucoptera sinuella* is revealed to be a mixture of 3,7-dimethylpentadecane, 3,7-dimethyltetradecane, and 7-methylpentadecane at a weight ratio of 95:2:3 (Non-Patent Literature 1).

Processes for synthesizing 3,7-dimethylpentadecane are reported, including, for example, the following process comprising a total of six steps (Non-Patent Literature 1). The hydroxyl group of citronellol is tosylated with p-toluenesulfonyl chloride in the presence of pyridine to obtain citronellyl tosylate, and citronellyl tosylate thus obtained is reduced with lithium aluminum hydride to synthesize 2,6-dimethyl-2-octene. Subsequently, 2,6-dimethyl-2-octene thus obtained is oxidized with selenium dioxide in the presence of dichloromethane and tert-butyl hydroperoxide to synthesize 2,6-dimethyl-2-octene-1-ol. 2,6-Dimethyl-2-octene-1-ol thus obtained is oxidized with pyridinium dichromate (PDC) in dichloromethane to synthesize 2,6-dimethyl-2-octenal. Next, 2,6-dimethyl-2-octenal thus obtained is subjected to a Wittig reaction with triphenylphosphonium heptylide prepared from heptyltriphenylphosphonium bromide and n-butyllithium to synthesize 3,7-dimethyl-6,8-pentadecadiene. Furthermore, 3,7-dimethyl-6,8-pentadecadiene thus obtained is hydrogenated with a palladium carbon catalyst to synthesize the target compound, 3,7-dimethylpentadecane.

Processes for preparing 3,7-dimethyltetradecane are reported, including, for example, the following process comprising a total of six steps (Non-Patent Literature 1). 2,6-Dimethyl-2-octenal is synthesized according to the afore-mentioned process for preparing 3,7-dimethylpentadecane. Next, 2,6-dimethyl-2-octenal thus obtained is subjected to a Wittig reaction with triphenylphosphonium hexylide prepared from hexyltriphenylphosphonium bromide and n-butyllithium to synthesize 3,7-dimethyl-6,8-tetradecadiene. Furthermore, 3,7-dimethyl-6,8-tetradecadiene thus obtained is hydrogenated with a palladium carbon catalyst to synthesize the target compound, 3,7-dimethyltetradecane.

LIST OF THE PRIOR ART

Non-Patent Literature

[Non-Patent Literature 1] Jan Bergmann et al., J. Chem. Ecol., 2020, 46 (9), 820-829.

Problems to be Solved by the Invention

Both of the processes for preparing 3,7-dimethylpentadecane and 3,7-dimethyltetradecane, respectively, described in Non-Patent Literature 1 use selenium dioxide, PDC and dichloromethane, which have extremely high environmental toxicity, and thus are undesirable in view of green chemistry. These processes also use tert-butyl hydroperoxide, which is explosive in a high purity, and n-butyllithium and palladium carbon, both of which are ignitable, making these processes difficult to be industrialized.

In addition, 3,7-dimethylpentadecane prepared according to the process described in Non-Patent Literature 1 contained 1.7% of 3,7-dimethyltetradecane and 1.3% of n-tetradecane as impurities and had a purity as low as 95%. The main impurities, 3,7-dimethyltetradecane having 16 carbon atoms and n-tetradecane having 14 carbon atoms, have a polarity close to that of the target compound, 3,7-dimethylpentadecane having 17 carbon atoms, and thus are difficult to separate them with each other using a column chromatography. Further, 3,7-dimethyltetradecane having 16 carbon atoms has a molecular weight and a boiling point close to those of 3,7-dimethylpentadecane having 17 carbon atoms, and thus they are difficult to separate them with each other using distillation. Therefore, it is difficult to prepare 3,7-dimethylpentadecane in a high purity using the preparation process described in Non-Patent Literature 1.

Likewise, 3,7-dimethyltetradecane prepared according to the process described in Non-Patent Literature 1 contained 1.3% of 3,7-dimethyltridecane and 1.1% of n-dodecane as impurities and had a purity as low as 96%. The main impurities, 3,7-dimethyltridecane having 15 carbon atoms and n-dodecane having 12 carbon atoms, have a polarity close to that of the target compound, 3,7-dimethyltetradecane having 16 carbon atoms, and thus are difficult to separate them with each other using a column chromatography. Further, 3,7-dimethyltridecane having 15 carbon atoms has a molecular weight and a boiling point close to those of the target compound, 3,7-dimethyltetradecane having 16 carbon atoms, and thus they are difficult to separate them with each other using distillation. Therefore, it is difficult to prepare 3,7-dimethyltetradecane in a high purity using the preparation process described in Non-Patent Literature 1.

SUMMARY OF THE INVENTION

However, both of the processes for preparing 3,7-dimethylpentadecane and 3,7-dimethyltetradecane, respectively, described in Non-Patent Literature 1 comprises total of six steps and thus the steps are too many.

The present invention has been made in the aforesaid circumstances and aims to provide processes for economically and efficiently preparing 3,7-dimethylpentadecane and 3,7-dimethyltetradecane, respectively.

As a result of the intensive researches to overcome the aforesaid problems of the prior art, the present inventors have found that it is possible to economically and efficiently prepare 3,7-dimethylpentadecane and 3,7-dimethyltetradecane, respectively, in a high purity via a coupling reaction between a nucleophilic reagent, 2,6-dimethyloctyl compound, and an electrophilic alkyl reagent, wherein the nucleophilic reagent, 2,6-dimethyloctyl compound, can be easily prepared from a 1-halo-2,6-dimethyloctane compound which can be inexpensively produced in a large amount, and the electrophilic alkyl reagent is inexpensively and industrially available. Thus, the present inventors have completed the present invention.

According to one aspect of the present invention, there is provided a process for preparing a 3,7-dimethylalkane compound of the following formula (3):

(3)

wherein n is 5 or 6, the process comprising:

subjecting a nucleophilic reagent, 2,6-dimethyloctyl compound, of the following general formula (1):

(1)

wherein $M^1$ represents Li, Mg $Z^1$, Cu$Z^1$, or CuLi$Z^1$, wherein $Z^1$ represents a halogen atom or a 2,6-dimethyloctyl group, to a coupling reaction with an electrophilic alkyl reagent of the following general formula (2):

(2)

wherein $X^1$ represents a halogen atom or a p-toluenesulfonate group, and n is as defined above, to form the 3,7-dimethylalkane compound (3).

According to another aspect of the present invention, there is provided a process for preparing a 3,7-dimethylalkane compound (3), the process further comprising:

subjecting a nucleophilic reagent, 3-methylpentyl compound, of the following general formula (4):

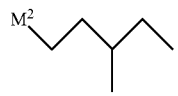
(4)

wherein $M^2$ represents Li, Mg$Z^2$, Cu$Z^2$, or CuLi$Z^2$, wherein $Z^2$ represents a halogen atom or a 3-methylpentyl group, to a coupling reaction with a 1,3-dihalo-2-methylpropane compound of the following general formula (5):

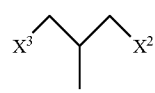
(5)

wherein $X^2$ and $X^3$ may be same with or different from each other and represent a halogen atom, to form a 1-halo-2,6-dimethyloctane compound of the following formula (6):

(6)

wherein $X^4$ represents a halogen atom, and preparing the nucleophilic reagent, 2,6-dimethyloctyl compound (1), from the 1-halo-2,6-dimethyloctane compound (6).

According to the present invention, 3,7-dimethylpentadecane and 3,7-dimethyltetradecane can be prepared, respectively, economically and efficiently with less environmental burden.

In the preparation of 3,7-dimethylpentadecane, tetradecane having 14 carbon atoms and 3,7,10,14-tetramethylhexadecane having 20 carbon atoms are by-produced as impurities. These impurities have boiling points different from that of the target compound 3,7-dimethylpentadecane having 17 carbon atoms. Accordingly, the target compound can be easily separated from the impurities with distillation, leading to the preparation of 3,7-dimethylpentadecane in a high purity.

Likewise, in the preparation of 3,7-dimethyltetradecane, dodecane having 12 carbon atoms and 3,7,10,14-tetramethylhexadecane having 20 carbon atoms are by-produced as impurities. These impurities have boiling points different from that of the target compound 3,7-dimethyltetradecane having 16 carbon atoms. Accordingly, the target compound can be easily separated from the impurities by distillation, leading to the preparation of 3,7-dimethyltetradecane in a high purity.

DETAILED DESCRIPTION OF THE INVENTION

I. A 3,7-dimethylalkane compound, which is a target compound of the present invention, of the following general formula (3) is prepared according to a process, as shown in the following chemical reaction formula. The preparation process comprises subjecting a nucleophilic reagent, 2,6-dimethyloctyl compound, of the following general formula (1) to a coupling reaction with an electrophilic alkyl reagent of the following general formula (2) to prepare the 3,7-dimethylalkane compound (3).

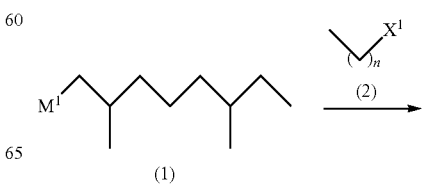

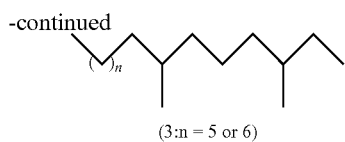

(3: n = 5 or 6)

First, the nucleophilic reagent, 2,6-dimethyloctyl compound (1), will be explained below.

$M^1$ in the general formula (1) represents Li, $MgZ^1$, $CuZ^1$, or $CuLiZ^1$, wherein $Z^1$ represents a halogen atom or a 2,6-dimethyloctyl group. Examples of the halogen atom $Z^1$ include a chlorine atom, a bromine atom, and an iodine atom.

Specific examples of the nucleophilic reagent, 2,6-dimethyloctyl compound (1), include 2,6-dimethyloctyl lithium; 2,6-dimethyloctylmagnesium halide reagents (i.e., Grignard reagent) such as 2,6-dimethyloctylmagnesium chloride, 2,6-dimethyloctylmagnesium bromide, and 2,6-dimethyloctylmagnesium iodide; bis[2,6-dimethyloctyl]cuprate; and a Gilman reagent such as lithium bis[2,6-dimethyloctyl]cuprate. 2,6-Dimethyloctylmagnesium halide reagents are preferred in view of the ease of the preparation and/or stability.

The nucleophilic reagent, 2,6-dimethyloctyl compound (1), may be used alone or in combination thereof. The nucleophilic reagent, 2,6-dimethyloctyl compound (1), may be commercially available one or may be prepared in house.

Next, the electrophilic alkyl reagent (2) will be explained below.

$X^1$ in the general formula (2) represents a halogen atom or a p-toluenesulfonate group (i.e., $CH_3$—$C_6H_6$—$SO_2$—O (TsO) group). Examples of the halogen atom $X^1$ include a chlorine atom, a bromine atom, and an iodine atom. A bromine atom and an iodine atom are particularly preferred.

"n" in the general formula (2) is 5 or 6.

Specific examples of the electrophilic alkyl reagent (2) include 1-halohexane compounds (n=5) such as 1-chlorohexane, 1-bromohexane, and 1-iodohexane; hexyl p-toluenesulfonate (n=5); 1-haloheptane compounds (n=6) such as 1-chloroheptane, 1-bromoheptane, and 1-iodoheptane; and heptyl p-toluenesulfonate (n=6). 1-Halohexane compounds (n=5) and 1-haloheptane compounds (n=6) are preferred in view of the ease of the preparation and/or stability.

The electrophilic alkyl reagent (2) may be used alone or in combination thereof. The electrophilic alkyl reagent (2) may be commercially available one or may be prepared in house.

Next, the coupling reaction between the nucleophilic reagent, 2,6-dimethyloctyl compound (1), and the electrophilic allyl reagent (2) will be explained below.

An amount of the nucleophilic reagent, 2,6-dimethyloctyl compound (1), used in the coupling reaction is preferably 0.8 to 1.2 mol, per mol of the electrophilic alkyl reagent (2) in view of the economy.

A solvent may be used in the coupling reaction, if necessary. Examples of the solvent include hydrocarbon solvents such as toluene, xylene, and hexane; ether solvents such as tetrahydrofuran, 4-methyltetrahydropyran, and diethyl ether; and polar solvents such as N,N-dimethylformamide, N,N-dimethylacetamide, N-methylpyrrolidone, dimethyl sulfoxide, γ-butyrolactone, and acetonitrile. Toluene, tetrahydrofuran, 4-methyltetrahydropyran, and acetonitrile, particularly tetrahydrofuran and 4-methyltetrahydropyran, are preferred in view of the reactivity.

The solvent may be used alone or in combination thereof. The solvent may be commercially available one.

An amount of the solvent used is preferably 30 to 5,000 g, more preferably 50 to 3,000 g, per mol of the nucleophilic reagent, 2,6-dimethyloctyl compound (1), in view of the reactivity.

A catalyst may be used in the coupling reaction, if necessary. Examples of the catalyst include cuprous halides such as cuprous chloride, cuprous bromide, and cuprous iodide; and cupric halides such as cupric chloride, cupric bromide, and cupric iodide. Cuprous halides, particularly cuprous iodide, are preferred in view of the reactivity.

The catalyst may be used alone or in combination thereof. The catalyst may be commercially available one.

An amount of the catalyst used is preferably 0.0003 to 0.300 mol, more preferably 0.001 to 0.100 mol, per mol of the nucleophilic reagent, 2,6-dimethyloctyl compound (1), in view of the reaction rate and/or post-treatment.

When the catalyst is used, a co-catalyst may also be incorporated, if necessary. Examples of the co-catalyst include phosphorus compounds including a trialkyl phosphite compound having 3 to 9 carbon atoms, such as triethyl phosphite, and a triaryl phosphine compound having 18 to 21 carbon atoms, such as triphenylphosphine. Trialkyl phosphite compounds are preferred in view of the reactivity.

The co-catalyst may be used alone or in combination thereof. The co-catalyst may be commercially available one.

An amount of the co-catalyst used is preferably 0.001 to 0.500 mol, more preferably 0.005 to 0200 mol, per mol of the nucleophilic reagent, 2,6-dimethyloctyl compound (1), in view of the reactivity.

When a catalyst is used in the coupling reaction, a lithium halide may also be incorporated, if necessary. Examples of the lithium halide include lithium chloride, lithium bromide, and lithium iodide. Lithium chloride is preferred in view of the reactivity.

An amount of the lithium halide used in the coupling reaction is preferably 0.005 to 0.250 mol, per mol of the electrophilic allyl reagent (2) in view of the reactivity.

A reaction temperature of the coupling reaction varies, depending on a nucleophilic reagent, 2,6-dimethyloctyl compound (1), to be used, and is preferably −78 to 70° C., more preferably −20 to 25° C., in view of the reactivity.

A reaction time of the coupling reaction varies, depending on a solvent to be used and/or a reaction scale, and is preferably 1 to 95 hours in view of the reactivity.

Next, the 3,7-dimethylalkane compound (3) will be explained below.

"n" in the general formula (3) is as defined for the general formula (2).

Specific examples of the 3,7-dimethylalkane compound (3) include 3,7-dimethylpentadecane (3: n=6) and 3,7-dimethyltetradecane (3: n=5).

In the step in which a coupling reaction for preparing a target compound of the present invention, 3,7-dimethylpentadecane (3: n=6), is carried out, tetradecane having 14 carbon atoms and 3,7,10,14-tetramethylhexadecane having 20 carbon atoms are by-produced as impurities. However, these impurities have boiling points different from that of the target compound, 3,7-dimethylpentadecane (3: n=6) having 17 carbon atoms. Accordingly, the target compound can be easily separated from the impurities with distillation, leading to the preparation of 3,7-dimethylpentadecane (3: n=6) in a high purity.

Likewise, in the step in which a coupling reaction for preparing a target compound of the present invention, 3,7-dimethyltetradecane (3: n=5) is carried out, dodecane having 12 carbon atoms and 3,7,10,14-tetramethylhexadecane having 20 carbon atoms are by-produced as impurities. However, these impurities have boiling points different from that of the target compound, 3,7-dimethyltetradecane (3: n=5) having 16 carbon atoms. Accordingly, the target compound can be easily separated from the impurities with distillation, leading to the preparation of 3,7-dimethyltetradecane (3: n=5) in a high purity.

II. A process for preparing the nucleophilic reagent, 2,6-dimethyloctyl compound (1), will be explained below.

The nucleophilic reagent, 2,6-dimethyloctyl compound (1), may be prepared in a conventional method or a process described below.

A process for preparing a nucleophilic reagent, 2,6-dimethyloctyl compound (1), for example, a 2,6-dimethyloctylmagnesium halide reagent (1: $M^1=MgZ^1$) will be explained below. The 2,6-dimethyloctylmagnesium halide reagent (1: $M^1=MgZ^1$) may be prepared, for example, by reacting a 1-halo-2,6-dimethyloctane compound of the following general formula (6) with magnesium in a solvent, as shown in the following chemical reaction formula.

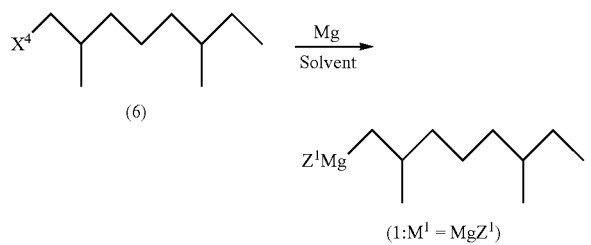

The 2,6-dimethyloctylmagnesium halide reagent (1: $M^1=MgZ^1$) is a Grignard reagent, wherein $Z^1$ is the same as $X^4$ and represents a halogen atom. Examples of the halogen atom $X^4$ include a chlorine atom, a bromine atom, and an iodine atom.

First, the 1-halo-2,6-dimethyloctane compound (6) will be explained below.

$X^4$ in the general formula (6) represents a halogen atom. Examples of the halogen atom $X^4$ include a chlorine atom, a bromine atom, and an iodine atom.

Specific examples of the 1-halo-2,6-dimethyloctane compound (6) include 1-chloro-2,6-dimethyloctane, 1-bromo-2,6-dimethyloctane, and 1-iodo-2,6-dimethyloctane.

The 1-halo-2,6-dimethyloctane compound (6) may be used alone or in combination thereof. The 1-halo-2,6-dimethyloctane compound (6) may be commercially available one or may be prepared in house.

An amount of magnesium used is preferably 1.0 to 2.0 gram atoms, per mol of the 1-halo-2,6-dimethyloctane compound (6) in view of the completion of the reaction.

Examples of the solvent include ether solvents such as tetrahydrofuran, diethyl ether, and 4-methyltetrahydropyran; and hydrocarbon solvents such as toluene, xylene, and hexane. Ethers such as tetrahydrofuran, diethyl ether, and 4-methyltetrahydropyran, particularly tetrahydrofuran and 4-methyltetrahydropyran, are preferred in view of a reaction rate of the Grignard reagent formation.

The solvent may be used alone or in combination thereof, if necessary. The solvent may be commercially available one.

An amount of the solvent used is preferably 30 to 5,000 g, more preferably 50 to 3,000 g, per mol of the 1-halo-2,6-dimethyloctane compound (6) in view of the reactivity.

A reaction temperature varies, depending on a solvent to be used, and is preferably 30 to 120° C. in view of the reactivity.

A reaction time varies, depending on a solvent to be used and/or a reaction scale, and is preferably 1 to 90 hours in view of the reactivity.

III. A process for preparing the 1-halo-2,6-dimethyloctane compound (6) will be explained below.

The 1-halo-2,6-dimethyloctane compound (6) may be prepared, for example, by subjecting a nucleophilic reagent, 3-methylpentyl compound, of the following general formula (4) to a coupling reaction with a 1,3-dihalo-2-methylpropane compound of the following general formula (5), as shown in the following chemical reaction formula.

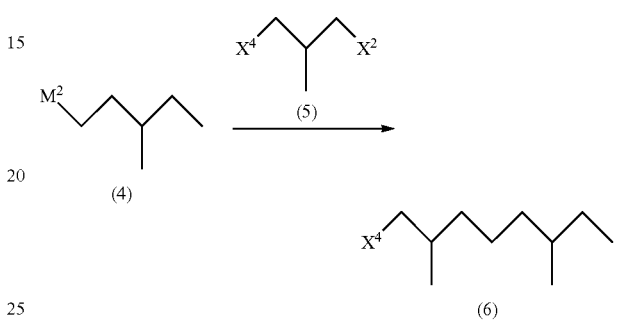

Next, the 1,3-dihalo-2-methylpropane compound (5) will be explained below.

$X^2$ and $X^3$ in the general formula (5) may be same with or different from each other and represent a halogen atom. Examples of the halogen atoms $X^2$ and $X^3$ include a chlorine atom, a bromine atom, and an iodine atom.

Examples of the combination of $X^2$ and $X^3$ include a chlorine atom and a chlorine atom; a bromine atom and a chlorine atom; a chlorine atom and an iodine atom; a bromine atom and a bromine atom; a bromine atom and an iodine atom; and an iodine atom and an iodine atom.

Specific examples of the 1,3-dihalo-2-methylpropane compound (5) include 1,3-dichloro-2-methylpropane, 1,3-dibromo-2-methylpropane, 1,3-diiodo-2-methylpropane, 1-bromo-3-chloro-2-methylpropane, 1-chloro-3-iodo-2-methylpropane, and 1-bromo-3-iodo-2-methylpropane. In view of the yield, 1-bromo-3-chloro-2-methylpropane, 1-chloro-3-iodo-2-methylpropane, and 1-bromo-3-iodo-2-methylpropane are particularly preferred.

The 1,3-dihalo-2-methylpropane compound (5) may be used alone or in combination thereof. The 1,3-dihalo-2-methylpropane compound (5) may be commercially available one or may be prepared in house.

The 1,3-dihalo-2-methylpropane compound (5) may be synthesized, for example, by halogenating 2-methyl-1,3-propanediol.

Next, the coupling reaction between the nucleophilic 3-methylpentyl reagent (4) and the 1,3-dihalo-2-methylpropane compound (5) will be explained below.

An amount of the nucleophilic 3-methylpentyl reagent (4) used in the coupling reaction is preferably 0.8 to 1.4 mol, per mol of the 1,3-dihalo-2-methylpropane compound (5) in view of the economy.

A solvent may be used in the coupling reaction, if necessary. Examples of the solvent include hydrocarbon solvents such as toluene, xylene, and hexane; ether solvents such as tetrahydrofuran, 4-methyltetrahydropyran, and diethyl ether; and polar solvents such as N,N-dimethylformamide, N,N-dimethylacetamide, N-methylpyrrolidone, dimethyl sulfoxide, γ-butyrolactone, and acetonitrile. Toluene, tetrahydrofuran, 4-methyltetrahydropyran, and acetonitrile, particularly tetrahydrofuran and 4-methyltetrahydropyran, are preferred in view of the reactivity.

The solvent may be used alone or in combination thereof. The solvent may be commercially available one.

An amount of the solvent used is preferably 30 to 5,000 g, more preferably 50 to 3,000 g, per mol of the 1,3-dihalo-2-methylpropane compound (5) in view of the reactivity.

A catalyst may be used in the coupling reaction, if necessary. Examples of the catalyst include cuprous halides such as cuprous chloride, cuprous bromide, and cuprous iodide; and cupric halides such as cupric chloride, cupric bromide, and cupric iodide. Cuprous halides, particularly cuprous iodide, are preferred in view of the reactivity.

The catalyst may be used alone or in combination thereof. The catalyst may be commercially available one.

An amount of the catalyst used is preferably 0.0003 to 0.3 mol, more preferably 0.001 to 0.1 mol, per mol of the 1,3-dihalo-2-methylpropane compound (5) in view of the reaction rate and/or post-treatment.

When the catalyst is used, a co-catalyst may also be incorporated, if necessary. Examples of the co-catalyst include phosphorus compounds including a trialkyl phosphite compound having 3 to 9 carbon atoms, such as triethyl phosphite; and a triaryl phosphine compounds having 18 to 21 carbon atoms, such as triphenylphosphine. Trialkyl phosphite compounds are preferred in view of the reactivity.

The co-catalyst may be used alone or in combination thereof. The co-catalyst may be commercially available one.

An amount of the co-catalyst used is preferably 0.001 to 0.500 mol, more preferably 0.005 to 0.100 mol, per mol of the 1,3-dihalo-2-methylpropane compound (5) in view of the reactivity.

When a catalyst is used in the coupling reaction, a lithium halide may also be incorporated, if necessary. Examples of the lithium halide include lithium chloride, lithium bromide, and lithium iodide. Lithium chloride is preferred in view of the reactivity.

An amount of the lithium halide used in the coupling reaction is preferably 0.005 to 0.250 mol, per mol of the 1,3-dihalo-2-methylpropane compound (5) in view of the reactivity.

A reaction temperature of the coupling reaction varies, depending on a nucleophilic reagent, 3-methylpentyl compound (4), to be used, and is preferably −78 to 70° C., more preferably −20 to 35° C. in view of the reactivity.

A reaction time of the coupling reaction varies, depending on a solvent to be used and/or a reaction scale, and is preferably 0.5 to 90 hours in view of the reactivity.

When $X^2$ and $X^3$ in the general formula (5) is different from each other, appropriate selection of a catalyst or a reaction temperature that will be explained below allows a more reactive halogen atom to react in the coupling reaction. For example, when a combination of $X^2$ and $X^3$ which are different from each other in a 1,3-dihalo-2-methylpropane compound (5) is a combination of a chlorine atom and a bromine atom or a combination of a chlorine atom and an iodine atom, $X^4$ in the 1-halo-2,6-dimethyloctane compound (6) would be a chlorine atom. When a combination of $X^2$ and $X^3$ which are different from each other in the 1,3-dihalo-2-methylpropane compound (5) is a combination of a bromine atom and an iodine atom, $X^4$ in the 1-halo-2,6-dimethyloctane compound (6) would be a bromine atom.

IV. A process for preparing the nucleophilic 3-methylpentyl reagent (4) will be explained below.

The nucleophilic 3-methylpentyl reagent (4) may be prepared in a conventional method or a process described below.

A process for preparing a nucleophilic reagent, 3-methylpentyl compound (4), for example, a 3-methylpentylmagnesium halide reagent (4: $M^2=MgZ^2$), will be explained below. The 3-methylpentylmagnesium halide reagent (4: $M^2=MgZ^2$) may be prepared, for example, by reacting a 1-halo-3-methylpentane compound of the following general formula (7) with magnesium in a solvent, as shown in the following chemical reaction formula.

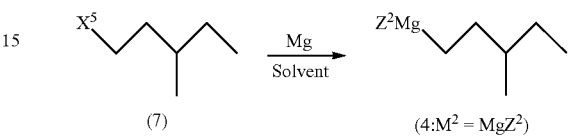

The 3-methylpentylmagnesium halide reagent (4: $M^2=MgZ^2$) is a Grignard reagent, wherein $Z^2$ is the same as $X^5$ and represents a halogen atom. Examples of the halogen atom $X^5$ include a chlorine atom, a bromine atom, and an iodine atom.

First, the 1-halo-3-methylpentane compound (7) will be explained below.

$X^5$ in the general formula (7) is as defined for the general formula (4: $M^2=MgZ^2$).

Specific examples of the 1-halo-3-methylpentane compound (7) include 1-chloro-3-methylpentane, 1-bromo-3-methylpentane, and 1-iodo-3-methylpentane.

The 1-halo-3-methylpentane compound (7) may be used alone or in combination thereof. The 1-halo-3-methylpentane compound (7) may be commercially available one or may be prepared in house.

An amount of magnesium used is preferably 1.0 to 2.0 gram atoms, per mol of the 1-halo-3-methylpentane compound (7) in view of the completion of the reaction.

Examples of the solvent include ether solvents such as tetrahydrofuran, diethyl ether, and 4-methyltetrahydropyran; and hydrocarbon solvents such as toluene, xylene, and hexane. Ethers such as tetrahydrofuran, diethyl ether, and 4-methyltetrahydropyran, particularly tetrahydrofuran and 4-methyltetrahydropyran, are preferred in view of a reaction rate of the Grignard reagent formation.

The solvent may be used alone or in combination thereof, if necessary. The solvent may be commercially available one.

An amount of the solvent used is preferably 30 to 5,000 g, more preferably 50 to 3,000 g, per mol of the 1-halo-3-methylpentane compound (7) in view of the reactivity.

A reaction temperature varies, depending on a solvent to be used, and is preferably 30 to 120° C. in view of the reactivity.

A reaction time varies, depending on a solvent to be used and/or a reaction scale, and is preferably 1 to 90 hours in view of the reactivity.

V. A process for preparing the 1-halo-3-methylpentane compound (7) will be explained below.

The 1-halo-3-methylpentane compound (7) may be prepared in a conventional method or a process described below.

The 1-halo-3-methylpentane compound (7) may be prepared, for example, by halogenating 3-methyl-1-pentanol of the following formula (8), as shown in the following chemical reaction formula.

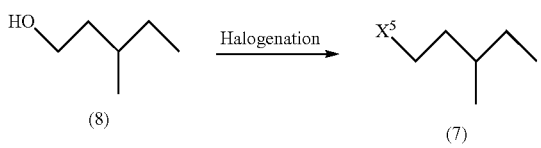

(8) → Halogenation → (7)

The halogenation reaction may be carried out, for example, by tosylating the hydroxyl group of 3-methyl-1-pentanol (8) with a p-toluenesulfonyl halide compound, followed by halogenation with a lithium halide compound, or by directly halogenating the hydroxyl group of 3-methyl-1-pentanol (8) with a halogenating agent.

Examples of the p-toluenesulfonyl halide compound include p-toluenesulfonyl chloride, p-toluenesulfonyl bromide, and p-toluenesulfonyl iodide.

Examples of the lithium halide compound include lithium chloride, lithium bromide, and lithium iodide.

Examples of the halogenating agent include halogen molecules such as chlorine, bromine, and iodine; hydrogen halide compounds such as hydrogen chloride, hydrogen bromide, and hydrogen iodide; methanesulfonyl halide compounds such as methanesulfonyl chloride, methanesulfonyl bromide, and methanesulfonyl iodide; benzenesulfonyl halide compounds such as benzenesulfonyl chloride, benzenesulfonyl bromide, and benzenesulfonyl iodide; p-toluenesulfonyl halide compounds such as p-toluenesulfonyl chloride, p-toluenesulfonyl bromide, and p-toluenesulfonyl iodide; phosphorus halide compounds such as phosphorous trichloride, phosphorous pentachloride, and phosphorus tribromide; carbon tetrahalide compounds such as carbon tetrachloride, carbon tetrabromide, and carbon tetraiodide; alkylsilyl halide compounds such as tetramethylsilyl chloride, tetramethylsilyl bromide, tetramethylsilyl iodide, triethylsilyl chloride, triethylsilyl bromide, triethylsilyl iodide, triisopropylsilyl chloride, triisopropylsilyl bromide, triisopropylsilyl iodide, tert-butyldimethylsilyl chloride, tert-butyldimethylsilyl bromide, and tert-butyldimethylsilyl iodide; oxalyl halide compounds such as oxalyl chloride, oxalyl bromide, and oxalyl iodide; N-halosuccinimide compounds such as N-chlorosuccinimide, N-bromosuccinimide, and N-iodosuccinimide; and thionyl chloride. Thionyl chloride, a methanesulfonyl halide compound, a benzenesulfonyl halide compound, and a p-toluenesulfonyl halide compound, particularly a methanesulfonyl halide compound, are preferred in view of the suppression of side reactions.

The halogenating agent may be used alone or in combination thereof, if necessary. The halogenating agent may be commercially available one.

An amount of the halogenating agent used is preferably 0.8 to 5.0 mol, more preferably 1.0 to 2.5 mol, per mol of 3-methyl-1-pentanol (8).

A base may be used in the halogenation reaction, if necessary.

Examples of the base include hydroxides such as sodium hydroxide, potassium hydroxide, calcium hydroxide, and magnesium hydroxide; carbonates such as sodium carbonate, potassium carbonate, calcium carbonate, and magnesium carbonate; amines such as triethylamine, N,N-diisopropylethylamine, piperidine, pyrrolidine, pyridine, lutidine, 4-dimethylaminopyridine, N,N-dimethylaniline, N,N-diethylaniline, and 1,8-diazabicyclo[5.4.0]-7-undecene (DBU); and phosphines such as tributylphosphine, triphenylphosphine, and tritolylphosphine.

When the halogenating agent is a methanesulfonyl halide compound, a benzenesulfonyl halide compound, or a p-toluenesulfonyl halide compound, the base is preferably an amine, more preferably pyridines such as pyridine, lutidine, or 4-dimethylaminopyridine.

The base may be used alone or in combination thereof, if necessary. The base may be commercially available one.

An amount of the base is preferably 0 to 8.0 mol, more preferably 0 to 3.0 mol, per mol of 3-methyl-1-pentanol (8) in view of the yield and economy.

A metal salt may be incorporated in the halogenation reaction, if necessary.

Examples of the metal salt include lithium salts such as lithium chloride, lithium bromide, and lithium iodide; sodium salts such as sodium chloride, sodium bromide, and sodium iodide; potassium salts such as potassium chloride, potassium bromide, and potassium iodide; calcium salts such as calcium chloride, calcium bromide, and calcium iodide; and magnesium salts such as magnesium chloride, magnesium bromide, and magnesium iodide.

The metal salt may be used alone or in combination thereof, if necessary. The metal salt may be commercially available one.

An amount of the metal salt used is preferably 0 to 30.0 mol, more preferably 0 to 5.0 mol, per mol of 3-methyl-1-pentanol (8) in view of the reactivity.

Although the metal salt increases a concentration of halide ions in the reaction system to enhance the reactivity, incorporation of the metal salt is unfavorable in view of the economy and/or environmental acceptability.

A solvent may be used in the halogenation reaction, if necessary.

Examples of the solvent include usual solvents, for example, ethers such as diethyl ether, dibutyl ether, 4-methyltetrahydropyran, tetrahydrofuran (THF), cyclopentyl methyl ether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone (GBL), N-methylpyrrolidone (NMP), N,N-dimethylformamide (DMF), N,N-dimethylacetamide (DMAC), and hexamethylphosphoric triamide (HMPA); nitriles such as acetonitrile and propionitrile; and esters such as methyl acetate, ethyl acetate, n-propyl acetate, and n-butyl acetate. 4-Methyltetrahydropyran, dichloromethane, chloroform, γ-butyrolactone, N-methylpyrrolidone, N,N-dimethylformamide, N,N-dimethylacetamide, and acetonitrile are preferred in view of the reactivity. γ-Butyrolactone and acetonitrile are particularly preferred in view of the safety.

The solvent may be used alone or in combination thereof, if necessary. The solvent may be commercially available one.

An amount of the solvent used is preferably 0 to 3,000 g, more preferably 0 to 800 g, per mol of 3-methyl-1-pentanol (8).

The solvent may occupy a part of a reactor space to result in reduction of a space for the starting materials, resulting in a decreased productivity. Therefore, the reaction may be carried out without a solvent or with the base as the solvent.

A reaction temperature of the halogenation reaction varies, depending on a p-toluenesulfonyl halide compound or a halogenating agent to be used, and is preferably −15 to 180° C., more preferably −5 to 100° C. in view of the reactivity.

A reaction time of the halogenation reaction varies, depending on a p-toluenesulfonyl halide compound or a halogenating agent to be used and/or a reaction scale, and is preferably 0.5 to 100 hours in view of the reactivity.

VI. A process for preparing 3-methyl-1-pentanol (8) will be explained below.

3-Methyl-1-pentanol (8) may be prepared in a conventional method or a process described below.

3-Methyl-1-pentanol (8) may be synthesized, for example, by subjecting a 2-halobutane compound (9) of the following general formula (9) to a reaction for preparing a Grignard reagent to form a sec-butylmagnesium halide compound (10) (which is a Grignard reagent) and reacting the sec-butylmagnesium halide compound (10) thus obtained with ethylene oxide to carry out a homologation reaction, as shown in the following chemical reaction formula.

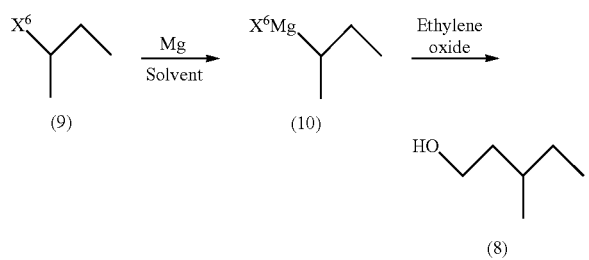

$X^6$ in the general formulae (9) and (10) represents a halogen atom. Examples of the halogen atom $X^6$ include a chlorine atom, a bromine atom, and an iodine atom.

First, the 2-halobutane compound (9) will be explained below.

Specific examples of the 2-halobutane compound (9) include 2-chlorobutane, 2-bromobutane, and 2-iodobutane.

An amount of magnesium used in the conversion with magnesium is preferably 1.0 to 2.0 gram atoms, per mol of the 2-halobutane compound (9) in view of the completion of the reaction.

The 2-halobutane compound (9) may be used alone or in combination thereof. The 2-halobutane compound (9) may be commercially available one or may be prepared in house.

Next, the conversion with magnesium will be explained below.

An amount of magnesium used is preferably 1.0 to 2.0 gram atoms, per mol of the 2-halobutane compound (9) in view of the completion of the reaction.

Examples of the solvent used in the conversion with magnesium include ethers such as tetrahydrofuran, diethyl ether, and 4-methyltetrahydropyran; and hydrocarbons such as toluene, xylene, and hexane. Ethers such as tetrahydrofuran, diethyl ether, and 4-methyltetrahydropyran, particularly tetrahydrofuran and 4-methyltetrahydropyran, are preferred in view of a reaction rate of the Grignard reagent formation.

The solvent may be used alone or in combination thereof, if necessary. The solvent may be commercially available one.

An amount of the solvent used is preferably 30 to 5,000 g, more preferably 50 g to 3,000 g, per mol of the 2-halobutane compound (9) in view of the reactivity.

A reaction temperature of the conversion with magnesium varies, depending on a solvent to be used, and is preferably 0 to 120° C. in view of the reactivity.

A reaction time of the conversion with magnesium varies, depending on a solvent to be used and/or a reaction scale, and is preferably 0.5 to 100 hours in view of the reactivity.

Next, the sec-butylmagnesium halide compound (10) will be explained below.

Specific examples of the sec-butylmagnesium halide compound (10) include sec-butylmagnesium chloride, sec-butylmagnesium bromide, and sec-butylmagnesium iodide.

Next, the homologation reaction will be explained below.

An amount of ethylene oxide used in the homologation reaction is preferably 1.0 to 10.0 mol, more preferably 1.0 to 3.0 mol, per mol of the 2-halobutane compound (9) in view of the reactivity.

A solvent may be used in the homologation reaction, if necessary. Examples of the solvent include usual solvents, for example, ethers such as diethyl ether, dibutyl ether, 4-methyltetrahydropyran, tetrahydrofuran (THF), cyclopentyl methyl ether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone (GBL), N-methylpyrrolidone, N,N-dimethylformamide, N,N-dimethylacetamide, and hexamethylphosphoric triamide; and nitriles such as acetonitrile and propionitrile. Ethers such as diethyl ether, tetrahydrofuran, and 4-methyltetrahydropyran are preferred in view of the reactivity.

The solvent may be used alone or in combination thereof, if necessary. The solvent may be commercially available one.

An amount of the solvent is preferably 30 to 5,000 g, more preferably 100 to 2,000 g, per mol of the 2-halobutane compound (9) in view of the reactivity.

A catalyst may be used in the homologation reaction, if necessary. Examples of the catalyst include cuprous halides such as cuprous chloride, cuprous bromide, and cuprous iodide; and cupric halides such as cupric chloride, cupric bromide, and cupric iodide. Cuprous halides, particularly cuprous chloride, are preferred in view of the reactivity.

The catalyst may be used alone or in combination thereof. The catalyst may be commercially available one.

An amount of the catalyst used is preferably 0.0003 to 0.300 mol, more preferably 0.0006 to 0.100 mol, per mol of the 2-halobutane compound (9) in view of the reaction rate and/or post-treatment.

EXAMPLES

The present invention will be described with reference to the following Examples. It should be noted that the present invention is not limited to or by the Examples.

The term "purity" as used herein means an area percentage in gas chromatography (GC), unless otherwise specified. The term "product ratio" means a ratio of area percentages in GC. The term "yield" is calculated from the area percentages determined by GC.

In the Examples, monitoring of the reactions and calculation of the yields were carried out in the following GC conditions.

GC conditions: GC: Capillary gas chromatograph GC-2014 (Shimadzu Corporation); column: DB-5, 0.25 μm×0.25 mmφ×30 m; carrier gas: He (1.55 mL/min), detector: FID; column temperature: 150° C., elevated in a rate of 5° C./min, and up to 230° C.

The yield was calculated according to the following equation in consideration of purities (% GC) of a starting material and a product.

Yield (%)={[(weight of a product obtained by a reaction×% GC)/molecular weight of a product] ÷[(weight of a starting material in a reaction×% GC)/molecular weight of a starting material]}× 100

THF represents tetrahydrofuran, GBL represents γ-butyrolactone, Et represents an ethyl group, and Ts represents a tosyl group.

Example 1: Preparation of 3-methyl-1-pentanol (8), a Starting Material for the Preparation of 1-chloro-3-methylpentane (7)

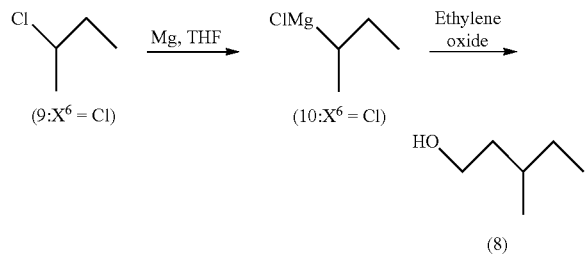

Magnesium (114.82 g, 4.73 gram atoms) and tetrahydrofuran (1350 g) were placed in a reactor at room temperature and stirred at 60 to 65° C. for 19 minutes. Next, 2-chlorobutane (9: $X^6$=Cl) (416.57 g, 4.50 mol) was added dropwise to the reactor at 60 to 75° C. After the completion of the dropwise addition, the reaction mixture was stirred at 75 to 80° C. for 2 hours to obtain sec-butylmagnesium chloride (10: $X^6$=Cl).

Subsequently, the reaction mixture was cooled to an internal temperature of 0 to 10° C., and cuprous chloride (0.94 g, 0.009 mol) was then added. The reaction mixture was stirred for 7 minutes. After the completion of the stirring, ethylene oxide was added dropwise at 0 to 10° C. After the completion of the dropwise addition, the reaction mixture was stirred at 0 to 10° C. for 1 hour. Next, an aqueous acetic acid solution (acetic acid (562.50 g) and water (1687.50 g)) were added to the reaction mixture, followed by layer separation. The aqueous layer was removed. The organic layer was concentrated at a reduced pressure, and the concentrate was subjected to distillation at a reduced pressure to obtain 3-methyl-1-pentanol (8) (404.11 g, 3.86 mol, purity 97.54%) in a yield of 85.73%.

The following is the spectrum data of 3-methyl-1-pentanol (8) thus prepared.

Nuclear magnetic resonance spectrum: $^1$H-NMR (500 MHz, CDCl$_3$): δ=0.86 (6H, t-like, J=7.3 Hz), 1.11-1.21 (1H, m), 1.30-1.40 (2H, m), 1.41-1.52 (1H, o-like), 1.55-1.63 (1H, m), 1.95 (1H, br·s), 3.84 (2H, t, J=5.0 Hz); $^{13}$C-NMR (500 MHz, CDCl$_3$): δ=11.2, 19.1, 29.5, 31.0, 39.4, 61.1.

Mass spectrum: EI-mass spectrum (70 eV): m/z 101 (M$^+$-1), 84, 69, 56, 41, 29.

Infrared absorption spectrum (D-ATR): ν=3333, 2962, 2929, 2876, 1463, 1379, 1059, 1031.

Example 2: Preparation of 1-chloro-3-methylpentane (7: $X^5$=Cl)

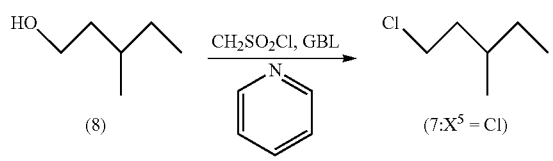

3-Methyl-1-pentanol (8) prepared in Example 1 (296.85 g, 2.83 mol, purity 97.54%), pyridine (336.25 g, 4.25 mol), and γ-butyrolactone (425.10 g) were placed in a reactor at room temperature and stirred at 40° C. for 15 minutes.

Subsequently, methanesulfonyl chloride (389.56 g, 3.40 mol) was added dropwise at 40 to 60° C. After the completion of the dropwise addition, the reaction mixture was heated to 60 to 65° C. and stirred for 7.5 hours. After the completion of the stirring, water (708.50 g) and hexane (425.10 g) were added, followed by phase separation. The aqueous layer was removed to obtain the organic layer. The organic layer was washed with an aqueous acetic acid solution (acetic acid (29.83 g) and water (372.89 g)) and then an aqueous sodium hydrogen carbonate solution (sodium hydrogen carbonate (14.92 g) and water (372.89 g)). The organic layer thus obtained was concentrated at a reduced pressure, and the concentrate was subjected to distillation at a reduced pressure to obtain 1-chloro-3-methylpentane (7: $X^5$=Cl) (291.29 g, 2.41 mol, purity 100%, b.p.=104.3 to 105.0° C./53.3 kPa (400.0 mmHg)) in a yield of 85.20%.

The following is the spectrum data of 1-chloro-3-methylpentane (7: $X^5$=Cl) thus prepared.

Nuclear magnetic resonance spectrum: $^1$H-NMR (500 MHz, CDCl$_3$): δ=0.88 (3H, t, J=6.5 Hz), 0.89 (3H, t, J=7.3 Hz), 1.18 (1H, sep-like, J=7.3 Hz), 1.32-1.41 (1H, m), 1.53-1.63 (2H, m), 1.75-1.84 (1H, sext-like, J=8.1 Hz), 3.50-3.61 (2H, m); $^{13}$C-NMR (500 MHz, CDCl$_3$): δ=11.1, 18.5, 29.1, 31.9, 39.4, 43.4.

Mass spectrum: ELI-mass spectrum (70 eV): m/z 120 (M$^+$), 84, 69, 57, 41, 29.

Infrared absorption spectrum (D-ATR): ν=2963, 2930, 2876, 1463, 1380, 1290, 724, 658.

Example 3: Preparation of 1-chloro-2,6-dimethyloctane (6: $X^4$=Cl)

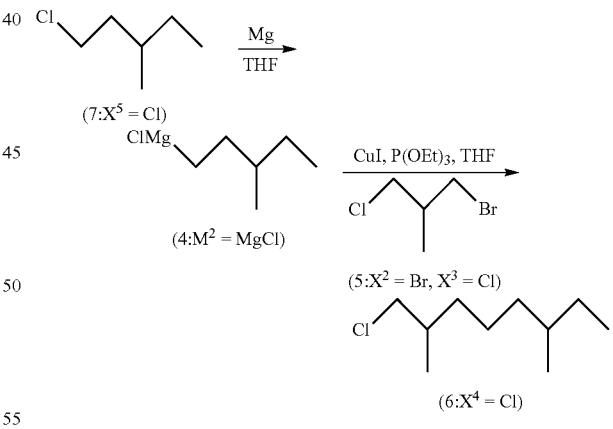

Magnesium (89.30 g, 3.67 gram atoms) and tetrahydrofuran (1050 g) were placed in a reactor at room temperature and stirred at 60 to 65° C. for 12 minutes. Next, 1-chloro-3-methylpentane prepared according to a process similar to that described in Example 2 (7: $X^5$=Cl) (422.89 g, 3.50 mol, purity: 99.83%) was added dropwise to the reactor at 60 to 75° C. After the completion of the dropwise addition, the reaction mixture was stirred at 75 to 80° C. for 2 hours to obtain 3-methylpentylmagnesium chloride (4: $M^2$=MgCl).

Subsequently, cuprous iodide (6.67 g, 0.035 mol), triethyl phosphite (13.96 g, 0.084 mol), tetrahydrofuran (350 g), and 1-bromo-3-chloro-2-methylpropane (5: $X^2$=Br, $X^3$=Cl) (558.10 g, 3.25 mol) were placed in another reactor, and then 3-methylpentylmagnesium chloride obtained above (4: $M^2$=MgCl) was added dropwise at 0 to 15° C. After the completion of the dropwise addition, the reaction mixture was stirred at 10 to 20° C. for 3 hours. Next, an aqueous ammonium chloride solution (ammonium chloride (35.00 g) and water (964.25 g)) and 20% by mass hydrochloric acid (33.50 g) were added to the reaction mixture, followed by phase separation. The organic layer thus obtained was subjected as such to distillation at a reduced pressure to obtain 1-chloro-2,6-dimethyloctane (6: $X^4$=Cl) (538.88 g, 2.89 mol, purity 94.78%, b.p.=116.1 to 117.2° C./5.3 kPa (40.0 mmHg)) in a yield of 88.77%. 1-Chloro-2,6-dimethyloctane thus obtained (6: $X^4$=Cl) contained 5.22% GC of 3,8-dimethyldecane having 12 carbon atoms.

The following is the spectrum data of 1-chloro-2,6-dimethyloctane (6: $X^4$=Cl) thus prepared.

Nuclear magnetic resonance spectrum: $^1$H-NMR (500 MHz, CDCl$_3$): δ=0.83-0.88 (6H, m), 1.00 (3H, dd, J=7.7 Hz, 1.2 Hz), 1.14-1.50 (9H, in), 1.76-1.86 (1H, o-like, J=6.5 Hz), 3.40 (1H, ddd, J=10.7 Hz, 6.5 Hz, 0.8 Hz), 3.48 (1H, ddd, J=10.7 Hz, 5.4 Hz, 1.9 Hz); $^{13}$C-NMR (500 MHz, CDCl$_3$): δ=11.4, 17.7, 17.8, 19.1, 19.2, 24.26, 24.28, 29.4, 29.5, 34.25, 34.31, 35.5, 36.6, 36.7, 51.26, 51.31.

Mass spectrum: EI-mass spectrum (70 eV): m/z 176 (M$^+$), 147, 111, 69, 57, 41, 29.

Infrared absorption spectrum (D-ATR): ν=2961, 2929, 2874, 1462, 1379, 730.

Example 4: Preparation of 3,7-dimethylpentadecane (3: n=6)

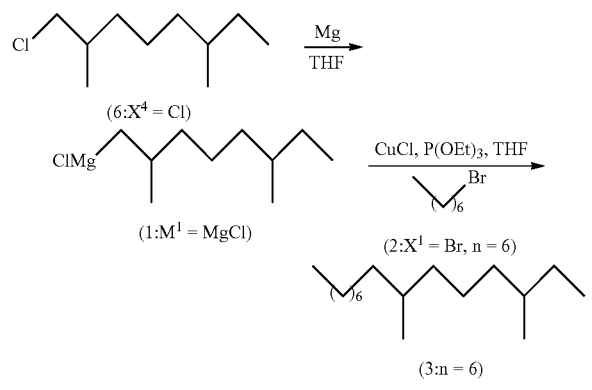

Magnesium (38.27 g, 1.58 gram atoms) and tetrahydrofuran (450 g) were placed in a reactor at room temperature and stirred at 60 to 65° C. for 10 minutes. Next, 1-chloro-2,6-dimethyloctane prepared in Example 3 (6: $X^4$=Cl) (279.70 g, 1.50 mol, purity: 94.78%) was added dropwise to the reactor at 60 to 75° C. After the completion of the dropwise addition, the reaction mixture was stirred at 75 to 80° C. for 2 hours to obtain 2,6-dimethyloctylmagnesium chloride (1: $M^1$=MgCl).

Subsequently, cuprous chloride (1.68 g, 0.017 mol), triethyl phosphite (16.82 g, 0.10 mol), lithium chloride (1.16 g, 0.027 mol), tetrahydrofuran (150 g), and 1-bromoheptane (2: $M^1$=Br, n=6) (268.65 g, 1.50 mol) were placed in another reactor, and then 2,6-dimethyloctylmagnesium chloride obtained above (1: $M^1$=MgCl) was added dropwise at 0 to 15° C. After the completion of the dropwise addition, the reaction mixture was stirred at 10 to 20° C. for 1.5 hours. Next, an aqueous ammonium chloride solution (ammonium chloride (15.0 g) and water (413.25 g)) and 20% by mass hydrochloric acid (24.36 g) were added to the reaction mixture, followed by layer separation. The organic layer thus obtained was subjected as such to distillation at a reduced pressure to obtain 3,7-dimethylpentadecane (3: n=6) (329.42 g, 1.36 mol, purity 99.57%, b.p.=125.3 to 131.5° C./0.4 kPa (3.0 mmHg)) in a yield of 90.90%. 3,7-Dimethylpentadecane (3: n=6) thus obtained contained 0.43% 3,7,10,14-tetramethylhexadecane having 20 carbon atoms, but tetradecane having 14 carbon atoms and 3,8-dimethyldecane having 12 carbon atoms were not detected by GC.

The organic layer at the completion of the reactions (which is the pre-distillation crude product) contained 47.20% 3,7-dimethylpentadecane (3: n=6), which is the target compound, 0.23% tetradecane, 1.58% 3,8-dimethyldecane, and 0.39% 3,7,10,14-tetramethylicosane, as determined by gas chromatography. This crude product was subjected to distillation at a reduced pressure. Tetradecane having 14 carbon atoms and 3,8-dimethyldecane having 12 carbon atoms were distilled off in the early stage of the distillation at a reduced pressure, and then 3,7-dimethylpentadecane having 17 carbon atoms (3: n=6) was distilled off in the middle stage of the distillation at a reduced pressure. As a result, highly pure 3,7-dimethylpentadecane (3: n=6) was produced. 3,7,10,14-Tetramethylhexadecane having 20 carbon atoms was concentrated and distilled off in the late stage of the distillation.

The following is the spectrum data of 3,7-dimethylpentadecane (3: n=6) thus prepared.

Nuclear magnetic resonance spectrum: $^1$H-NMR (500 MHz, CDCl$_3$): δ=0.80-0.95 (m, 12H), 1.0-1.45 (m, 24H); $^{13}$C-NMR (500 MHz, CDCl$_3$): δ=11.40, 11.43, 14.12, 19.21, 19.26, 19.70, 19.76, 22.71, 24.51, 27.11, 29.38, 29.48, 29.59, 29.71, 30.05, 31.95, 32.7.

Mass spectrum: EI-mass spectrum (70 eV): m/z 240 (M$^+$), 211, 183, 140, 127, 113, 97, 85, 71, 57, 43, 29.

Infrared absorption spectrum (D-ATR): ν=2958, 2925, 2872, 2855, 1463, 1377.

Example 5: Preparation of 3,7-dimethyltetradecane (3: n=5)

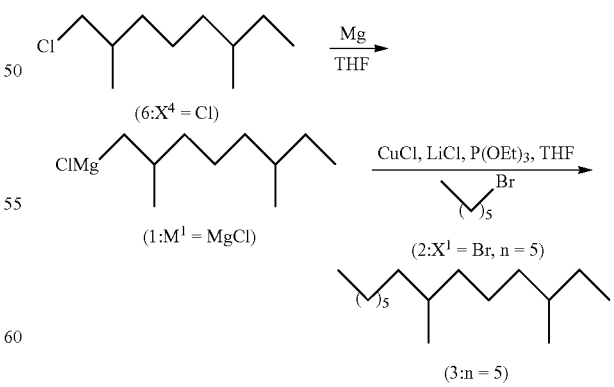

Magnesium (25.52 g, 1.05 gram atoms) and tetrahydrofuran (300 g) were placed in a reactor at room temperature and stirred at 60 to 65° C. for 14 minutes. Next, 1-chloro-2,6-dimethyloctane prepared in Example 3 (6: $X^4$=Cl)

(186.46 g, 1.00 mol, purity: 94.78%) was added dropwise to the reactor at 60 to 75° C. After the completion of the dropwise addition, the reaction mixture was stirred at 75 to 80° C. for 2 hours to obtain 2,6-dimethyloctylmagnesium chloride (1: $M^1$=MgCl).

Subsequently, cuprous chloride (1.12 g, 0.011 mol), triethyl phosphite (11.22 g, 0.068 mol), lithium chloride (0.78 g, 0.018 mol), tetrahydrofuran (100 g), and 1-bromohexane (2: $M^1$=Br, n=5) (165.07 g, 1.00 mol) were placed in another reactor, and then 2,6-dimethyloctylmagnesium chloride obtained above (1: $M^1$=MgCl) was added dropwise at 0 to 15° C. After the completion of the dropwise addition, the reaction mixture was stirred at 10 to 20° C. for 2 hours. Next, an aqueous ammonium chloride solution (ammonium chloride (10.0 g) and water (275.50 g)) and 20% by mass hydrochloric acid (9.57 g) were added to the reaction mixture, followed by layer separation. The organic layer thus obtained was subjected as such to distillation at a reduced pressure to obtain 3,7-dimethyltetradecane (3: n=5) (226.85 g, 1.00 mol, purity 99.82%, b.p.=127.7 to 127.8° C./0.4 kPa (3.0 mmHg)) in a yield of 100%. When 3,7-dimethyltetradecane thus obtained (3: n=5) was analyzed by GC, 3,7,10,14-tetramethylhexadecane having 20 carbon atoms, dodecane having 12 carbon atoms, and 3,8-dimethyldecane having 12 carbon atoms were not detected.

The organic layer at the completion of the reactions (which is the pre-distillation crude product) contained 42.15% 3,7-dimethyltetradecane (3: n=5), which is the target compound, 0.29% dodecane, 1.49% 3,8-dimethyldecane, and 0.46% 3,7,10,14-tetramethylhexadecane, as determined by GC. This crude product was subjected to distillation at a reduced pressure. Dodecane having 12 carbon atoms and 3,8-dimethyldecane having 12 carbon atoms were distilled off in the early stage of the distillation at a reduced pressure, and then 3,7-dimethyltetradecane having 16 carbon atoms (3: n=5) was distilled off in the middle stage of the distillation at a reduced pressure. As a result, highly pure 3,7-dimethyltetradecane (3: n=5) was produced. 3,7,10,14-Tetramethylhexadecane having 20 carbon atoms was not distilled off.

The following is the spectrum data of 3,7-dimethyltetradecane (3: n=5) thus prepared.

Nuclear magnetic resonance spectrum: $^1$H-NMR (500 MHz, CDCl$_3$): δ=0.82-0.95 (m, 12H, 1.0-1.45 (22H); $^{13}$C-NMR (500 MHz, CDCl$_3$): δ=11.43, 14.12, 19.21, 19.26, 19.76, 22.72, 24.51, 27.12, 29.42, 29.49, 29.59, 30.01, 31.95, 32.78, 32.80, 34.43, 36.9.

Mass spectrum: EI-mass spectrum (70 eV): m/z 226 (M$^+$), 197, 169, 126, 97, 85, 71, 57, 43, 29.

Infrared absorption spectrum (D-ATR): ν=2958, 2925, 2872, 2855, 1463, 1377.

Example 6: Preparation of 3,7-dimethylpentadecane (3: n=6)

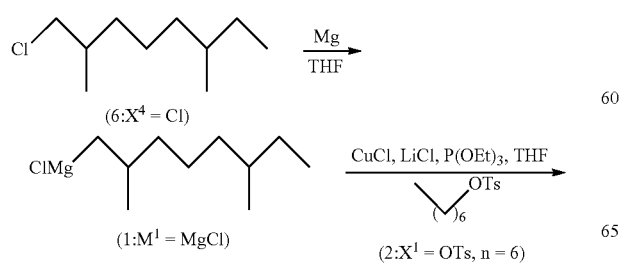

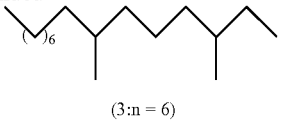

(3: n = 6)

Magnesium (2.49 g, 0.10 gram atoms) and tetrahydrofuran (29.26 g) were placed in a reactor at room temperature and stirred at 60 to 65° C. for 36 minutes. Next, 1-chloro-2,6-dimethyloctane prepared in Example 3 (6: $X^4$=Cl) (18.18 g, 0.098 mol, purity: 94.78%) was added dropwise to the reactor at 60 to 75° C. After the completion of the dropwise addition, the reaction mixture was stirred at 75 to 80° C. for 2 hours to obtain 2,6-dimethyloctylmagnesium chloride (1: $M^1$=MgCl).

Subsequently, cuprous chloride (0.11 g, 0.0011 mol), triethyl phosphite (1.09 g, 0.0066 mol), lithium chloride (0.076 g, 0.0018 mol), tetrahydrofuran (9.75 g), and hexyl p-toluenesulfonate (2: $X^1$=OTs, n=6) (25.00 g, 0.098 mol) were placed in another reactor, and then 2,6-dimethyloctylmagnesium chloride (1: $M^1$=MgCl) obtained above was added dropwise at 0 to 15° C. After the completion of the dropwise addition, the reaction mixture was stirred at 10 to 20° C. for 1.5 hours. Next, an aqueous ammonium chloride solution (ammonium chloride (0.98 g) and water (26.87 g)) and 20% by mass hydrochloric acid (0.93 g) were added to the reaction mixture, followed by filtration and then layer separation. The organic layer thus obtained was subjected as such to distillation at a reduced pressure to obtain 3,7-dimethylpentadecane (3: n=6) (20.32 g, 0.089 mol, purity 99.33%, b.p.=125.3 to 131.5° C./0.4 kPa (3.0 mmHg)) in a yield of 91.40%. 3,7-Dimethylpentadecane thus obtained (3: n=6) contained 0.42% 3,7,10,14-tetramethylhexadecane having 20 carbon atoms, but tetradecane having 14 carbon atoms and 3,8-dimethyldecane having 12 carbon atoms were not detected by GC.

The organic layer at the completion of the reactions (which is the pre-distillation crude product) contained 46.20% 3,7-dimethylpentadecane (3: n=6), which is the target compound, 0.33% tetradecane, 1.78% 3,8-dimethyldecane, and 0.40% 3,7,10,14-tetramethylicosane, as determined by GC. This crude product was subjected to distillation at a reduced pressure. Tetradecane having 14 carbon atoms and 3,8-dimethyldecane having 12 carbon atoms were distilled off in the early stage of the distillation at a reduced pressure, and then 3,7-dimethylpentadecane having 17 carbon atoms (3: n=6) was distilled off in the middle stage of the distillation at a reduced pressure. As a result, highly pure 3,7-dimethylpentadecane (3: n=6) was produced. 3,7,10,14-Tetramethylhexadecane having 20 carbon atoms was concentrated and distilled off in the late stage of the distillation.

Various spectrum data of 3,7-dimethylpentadecane (3: n=6) thus prepared were the same as those obtained in Example 4.

The invention claimed is:

1. A process for preparing a 3,7-dimethylalkane compound of the following formula (3):

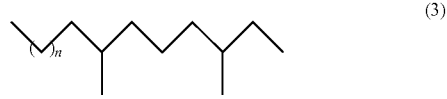

(3)

wherein n is 5 or 6,
the process comprising:
  subjecting a nucleophilic reagent, 2,6-dimethyloctyl compound, of the following general formula (1):

(1)

wherein $M^1$ represents Li, Mg $Z^1$, $CuZ^1$, or $CuLiZ^1$, wherein $Z^1$ represents a halogen atom or a 2,6-dimethyloctyl group, to a coupling reaction with an electrophilic alkyl reagent of the following general formula (2):

(2)

wherein $X^1$ represents a halogen atom or a p-toluenesulfonate group, and n is as defined above,
to form the 3,7-dimethylalkane compound (3).

2. The process for preparing a 3,7-dimethylalkane compound (3) according to claim 1, the process further comprising:
  subjecting a nucleophilic reagent, 3-methylpentyl compound, of the following general formula (4):

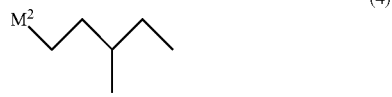
(4)

wherein $M^2$ represents Li, $MgZ^2$, $CuZ^2$, or $CuLiZ^2$, wherein $Z^2$ represents a halogen atom or a 3-methylpentyl group, to a coupling reaction with a 1,3-dihalo-2-methylpropane compound of the following general formula (5):

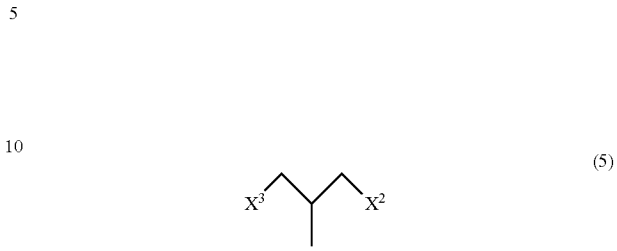
(5)

wherein $X^2$ and $X^3$ may be same with or different from each other and represent a halogen atom,
to form a 1-halo-2,6-dimethyloctane compound of the following formula (6):

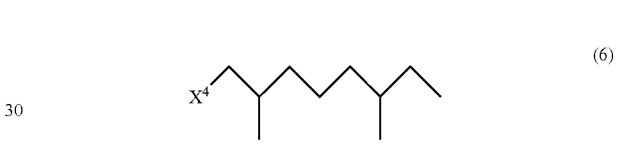
(6)

wherein $X^4$ represents a halogen atom, and
  preparing the nucleophilic reagent, 2,6-dimethyloctyl compound (1), from the 1-halo-2,6-dimethyloctane compound (6).

* * * * *